(12) United States Patent
Ding et al.

(10) Patent No.: US 10,779,880 B2
(45) Date of Patent: Sep. 22, 2020

(54) SURGICAL FORCEPS FOR GRASPING, TREATING, AND/OR CUTTING TISSUE

(71) Applicant: COVIDIEN LP, Mansfield, MA (US)

(72) Inventors: Weijiang Ding, Shanghai (CN); Mingfeng Xu, Hefei (CN)

(73) Assignee: Covidien LP, Mansfield, MA (US)

( * ) Notice: Subject to any disclaimer, the term of this patent is extended or adjusted under 35 U.S.C. 154(b) by 235 days.

(21) Appl. No.: 15/516,711

(22) PCT Filed: Oct. 22, 2014

(86) PCT No.: PCT/CN2014/089142
§ 371 (c)(1),
(2) Date: Apr. 4, 2017

(87) PCT Pub. No.: WO2016/061752
PCT Pub. Date: Apr. 28, 2016

(65) Prior Publication Data
US 2017/0296212 A1    Oct. 19, 2017

(51) Int. Cl.
*A61B 18/14* (2006.01)
*A61B 17/295* (2006.01)
*A61B 17/32* (2006.01)
*A61B 17/29* (2006.01)
*A61B 18/00* (2006.01)

(52) U.S. Cl.
CPC ........ *A61B 18/1445* (2013.01); *A61B 17/295* (2013.01); *A61B 2017/2929* (2013.01); *A61B 2017/2936* (2013.01); *A61B 2017/320069* (2017.08); *A61B 2018/00601* (2013.01);
(Continued)

(58) Field of Classification Search
CPC .............. A61B 17/295; A61B 18/1445; A61B 2018/1452
See application file for complete search history.

(56) References Cited

U.S. PATENT DOCUMENTS 5,290,286 A    3/1994  Parins
5,810,805 A *  9/1998  Sutcu ................. A61B 18/1442
                                                        606/45

(Continued)

*Primary Examiner* — Eun Hwa Kim
*Assistant Examiner* — Catherine Premraj
(74) *Attorney, Agent, or Firm* — Carter, DeLuca & Farrell LLP

(57) ABSTRACT

An end effector assembly for a forceps includes first and second jaw members each having an opposed electrically-conductive tissue-contacting surface. The first jaw member is pivotable relative to the second jaw member between a spaced-apart position and an approximated position for grasping tissue between the opposed electrically-conductive tissue-contacting surfaces. The second jaw member includes an electrical cutting element and is translatable relative to the first jaw member between a first position, wherein the opposed electrically-conductive tissue-contacting surfaces are aligned with one another, and a second position, wherein the opposed electrically-conductive tissue-contacting surfaces are longitudinally offset relative to one another. Upon translation of the second jaw member between the first and second positions, the electrical cutting element is translated at least partially along the opposed electrically-conductive tissue-contacting surface of the first jaw member.

20 Claims, 8 Drawing Sheets

(52) U.S. Cl.
CPC ............. *A61B 2018/1452* (2013.01); *A61B 2018/1455* (2013.01)

(56) References Cited

U.S. PATENT DOCUMENTS

| | | | | |
|---|---|---|---|---|
| 6,024,744 | A * | 2/2000 | Kese | A61B 18/1445 606/45 |
| 6,190,386 | B1 | 2/2001 | Rydell | |
| 6,273,887 | B1 * | 8/2001 | Yamauchi | A61B 18/1442 606/48 |
| 6,656,177 | B2 | 12/2003 | Truckai et al. | |
| 7,232,440 | B2 * | 6/2007 | Dumbauld | A61B 18/1445 606/45 |
| 7,445,621 | B2 * | 11/2008 | Dumbauld | A61B 18/1445 606/41 |
| 7,625,370 | B2 | 12/2009 | Hart et al. | |
| 8,512,359 | B2 | 8/2013 | Whitman et al. | |
| 2002/0183734 | A1 * | 12/2002 | Bommannan | A61B 18/1445 606/32 |
| 2005/0090817 | A1 * | 4/2005 | Phan | A61B 18/1445 606/41 |
| 2011/0186614 | A1 | 8/2011 | Kasvikis | |
| 2013/0334280 | A1 | 12/2013 | Krehel et al. | |
| 2014/0276738 | A1 * | 9/2014 | Price | A61B 17/2909 606/33 |

* cited by examiner

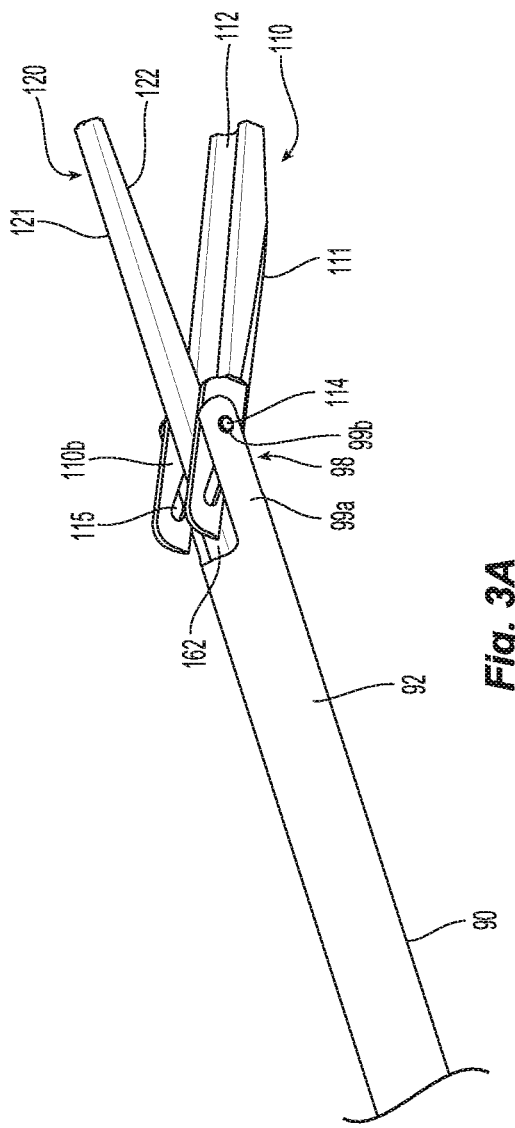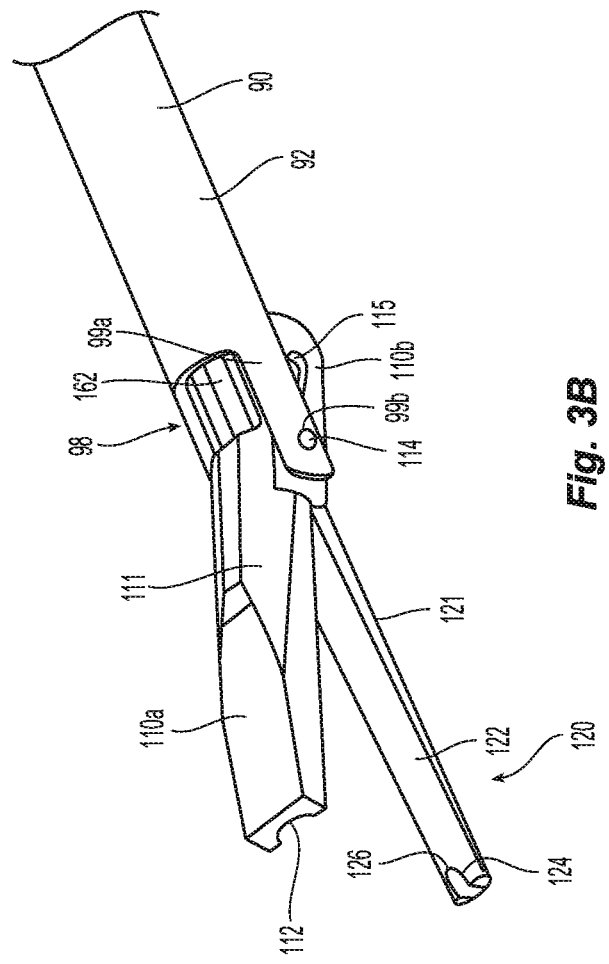

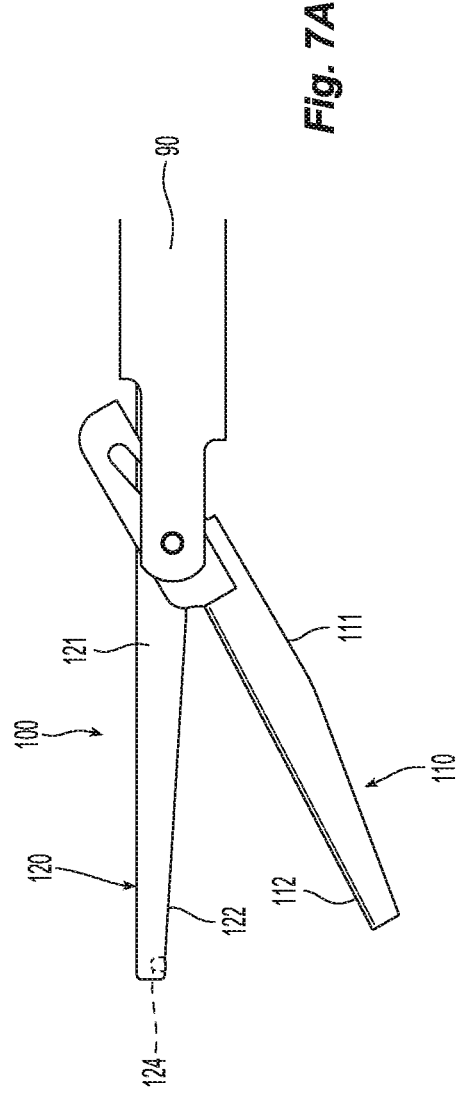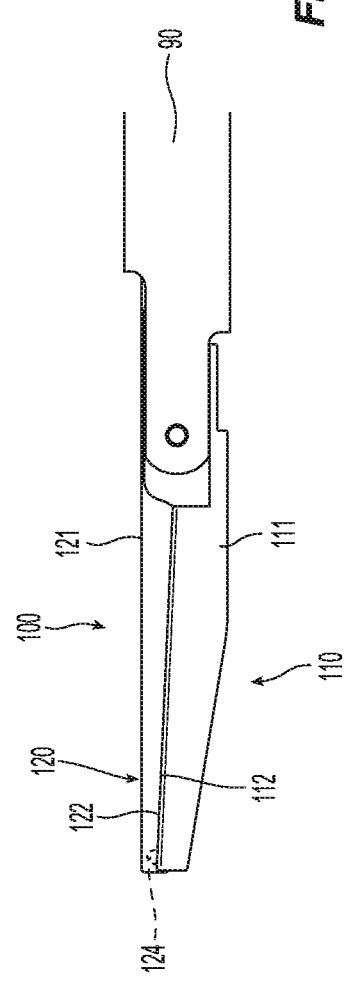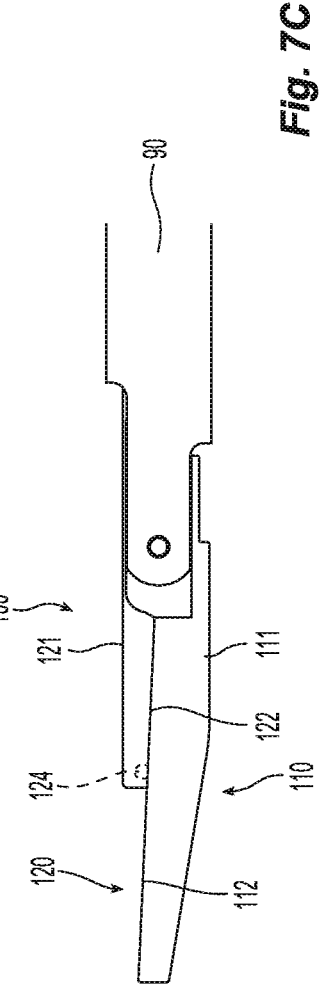

SURGICAL FORCEPS FOR GRASPING, TREATING, AND/OR CUTTING TISSUE

CROSS REFERENCE TO RELATED APPLICATION

The present application is a U.S. National Stage Application under 35 U.S.C. § 371(a) of PCT/CN2014/089142 filed Oct. 22, 2014, the entire contents of which are incorporated by reference herein.

BACKGROUND

Technical Field

The present disclosure relates generally to surgical instruments and, more particularly, to surgical forceps for grasping, treating, and/or cutting tissue.

Background of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to treat, e.g., cauterize, coagulate/desiccate, and/or seal, tissue. Typically, once tissue is treated, the surgeon has to accurately sever the treated tissue. Accordingly, many instruments have been designed which incorporate a knife or blade member which effectively severs the tissue after tissue treatment. Alternatively or additionally, energy-based tissue division may be effected.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with aspects of the present disclosure, a forceps is provided including an end effector assembly having first and second jaw members. Each jaw member includes an opposed electrically-conductive tissue-contacting surface. The first jaw member is pivotable relative to the second jaw member between a spaced-apart position and an approximated position for grasping tissue between the opposed electrically-conductive tissue-contacting surfaces thereof. The second jaw member includes an electrical cutting element and is translatable relative to the first jaw member between a first position, wherein the opposed electrically-conductive tissue-contacting surfaces are aligned with one another, and a second position, wherein the opposed electrically-conductive tissue-contacting surfaces are longitudinally offset relative to one another. Upon translation of the second jaw member between the first and second positions, the electrical cutting element is translated at least partially along the opposed electrically-conductive tissue-contacting surface of the first jaw member.

In an aspect of the present disclosure, the opposed electrically-conductive tissue-contacting surfaces of the first and second jaw members are adapted to connect to a source of energy for conducting energy through tissue grasped therebetween to treat tissue.

In another aspect of the present disclosure, the electrical cutting element is adapted to connect to a source of energy for conducting energy through tissue for dynamic electrical tissue cutting. More specifically, the electrical cutting element may be configured for monopolar dynamic electrical tissue cutting or, in conjunction with one or both of the opposed electrically-conductive tissue-contacting surfaces, may be configured for bipolar dynamic electrical tissue cutting.

In still another aspect of the present disclosure, the first and second jaw members define complementary configurations. In particular, the second jaw member may define an oval cross-sectional shape and the first jaw member may define a concave recess having a semi-oval cross-sectional shape. In such aspects, the recess of the first jaw member is configured to at least partially receive the second jaw member in the approximated position of the first jaw member.

In still yet another aspect of the present disclosure, in the second position of the second jaw member, between 25% and 75% of the opposed electrically-conductive tissue-contacting surfaces are disposed in non-overlapping relation relative to one another. In particular, in aspects, in the second position of the second jaw member, 50% of the opposed electrically-conductive tissue-contacting surfaces are disposed in non-overlapping relation relative to one another.

Another forceps provided in accordance with aspects of the present disclosure includes a housing, a shaft extending distally from the housing, an end effector assembly disposed at a distal end of the shaft, and first and second drive assemblies. The end effector assembly may be configured similarly to any of the end effector assemblies detailed above or any of the other aspects detailed herein. The first drive assembly is coupled to the first jaw member and selectively operable to pivot the first jaw member relative to the second jaw member between the spaced-apart and approximated positions. The second drive assembly is coupled to the second jaw member and selectively operable to translate the second jaw member relative to the first jaw member between the first and second positions.

In an aspect of the present disclosure, the forceps further includes a handle assembly associated with the housing and operably coupled to the first drive assembly. The handle assembly includes a movable handle that is movable between an initial position and a compressed position to pivot the first jaw member relative to the second jaw member between the spaced-apart and approximated positions.

In another aspect of the present disclosure, the forceps further includes a trigger assembly associated with the housing and operably coupled to the second drive assembly. The trigger assembly includes a trigger movable between an un-actuated position and an actuated position to translate the second jaw member relative to the first jaw member between the first and second positions.

In yet another aspect of the present disclosure, the forceps further includes a rotating assembly coupled to the first and second drive assemblies and the shaft. The rotating assembly includes a rotation wheel selectively rotatable relative to the housing for rotating the shaft and end effector assembly relative to the housing.

In still another aspect of the present disclosure, the forceps further includes an activation button disposed on the housing. The activation button is selectively actuatable for initiating the supply of energy to the opposed electrically-conductive tissue-contacting surfaces of the first and second jaw members and/or to the electrical cutting element.

BRIEF DESCRIPTION OF THE DRAWINGS

Various aspects and features of the present disclosure are described hereinbelow with reference to the drawings wherein like reference numerals identify similar or identical elements:

FIG. 3A is an enlarged, rear, perspective view of the distal end of the forceps of FIG. 1, with the end effector assembly disposed in a spaced-apart position;

FIG. 3B is an enlarged, front, perspective view of the distal end of the forceps of FIG. 1, with the end effector assembly disposed in the spaced-apart position;

FIG. 7A is an enlarged, side view of the area of detail indicates as "7A" in FIG. 4;

FIG. 7B is an enlarged, side view of the area of detail indicates as "7B" in FIG. 5;

FIG. 7C is an enlarged, side view of the area of detail indicates as "7C" in FIG. 6.

DETAILED DESCRIPTION

Figure 1:
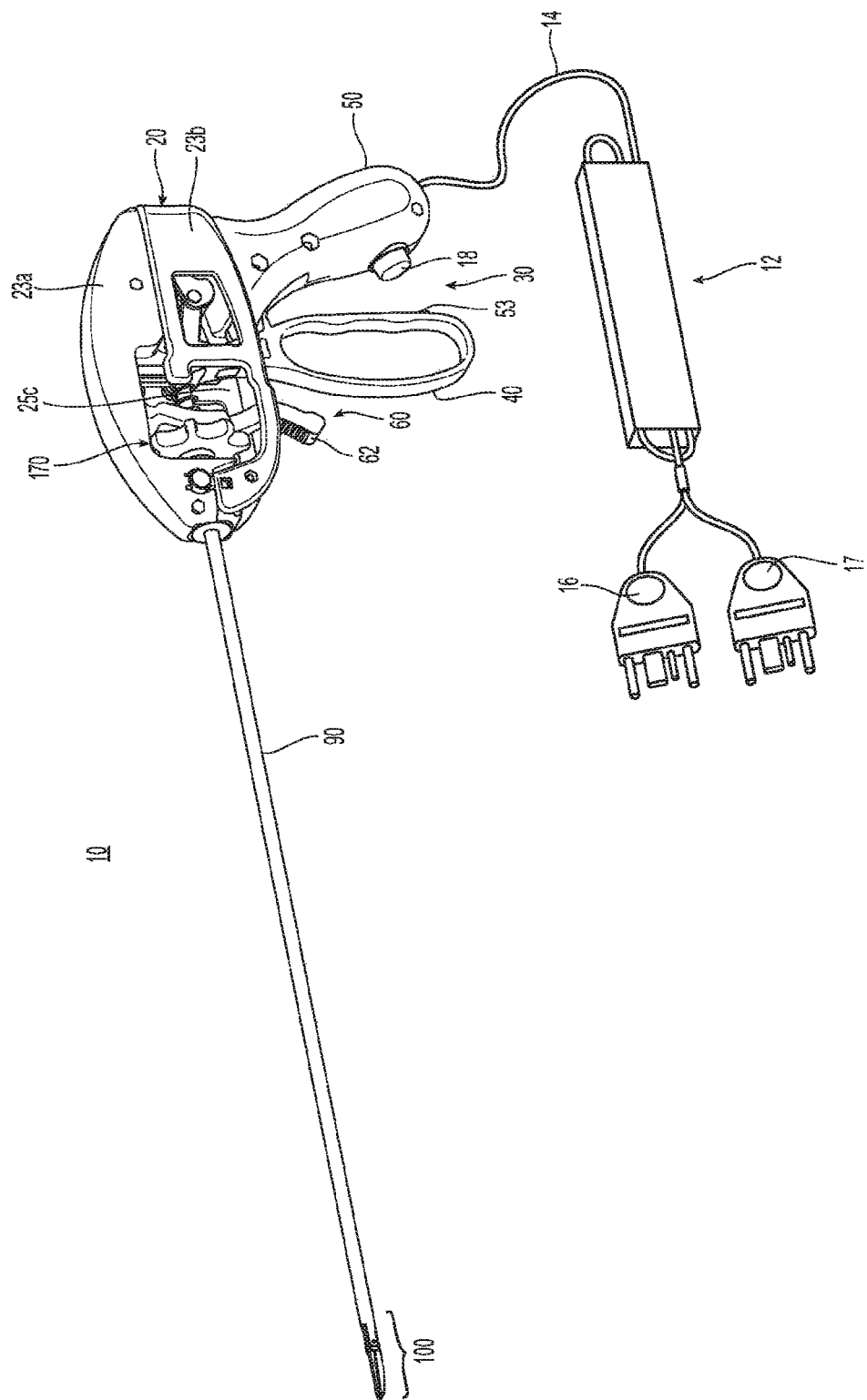
FIG. 1 is a perspective view of an endoscopic surgical forceps provided in accordance with the present disclosure.

Turning to FIGS. 1-7C, an endoscopic surgical forceps provided in accordance with the present disclosure is shown generally identified by reference numeral 10. As detailed below, forceps 10 is configured for selectively grasping, treating, and/or cutting tissue and generally includes an electrical connector assembly 12, a housing 20, a handle assembly 30, a trigger assembly 60, and a transmission assembly 80 which includes an outer shaft 90, an end effector assembly 100, a first drive assembly 130, a second drive assembly 160, and a rotating assembly 170. Electrical connector assembly 12 includes a cable 14 that houses a plurality of electrical leads 15, and at least one plug 16, 17 disposed at the free end of cable 14 for connecting cable 14 to a source of energy, e.g., a generator (not shown), for supplying energy to forceps 10, although forceps 10 may alternatively be configured as a handheld battery-powered instrument. An activation button 18 is operably positioned on forceps 10 to enable forceps 10 to selectively supply energy to tissue, as detailed below.

Figure 2:
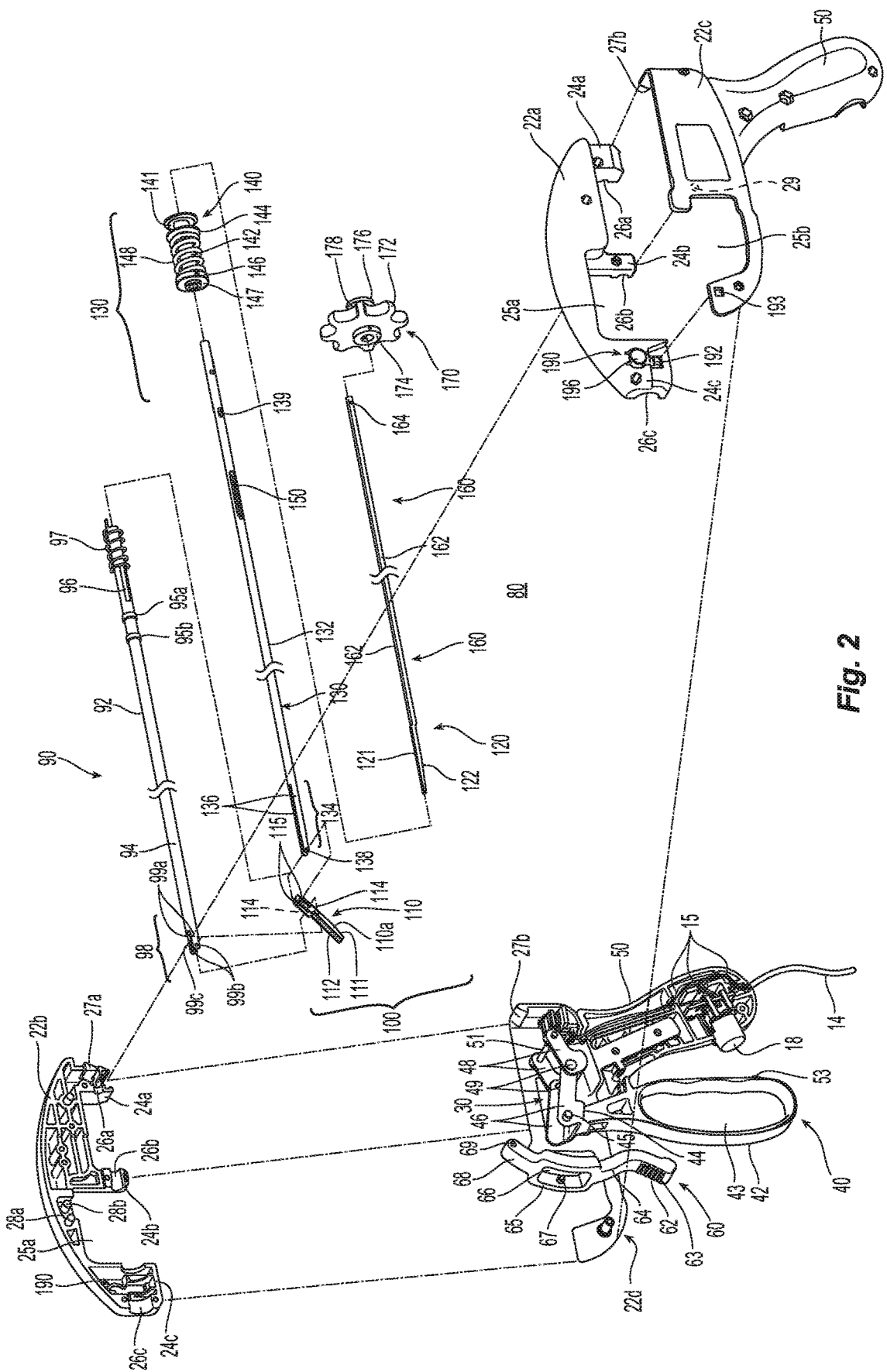
FIG. 2 is an exploded, perspective view of the forceps of FIG. 1.

Referring to FIGS. 1 and 2, housing 20 of forceps 10 is formed from a plurality of housing components, e.g., four housing components 22a, 22b, 22c, 22d, that cooperate to operably retain at least a portion of handle assembly 30, trigger assembly 60, and transmission assembly 80 therein. Although four (4) housing components 22a, 22b, 22c, 22d are shown, a greater or fewer number of housing components and/or different configurations thereof are also contemplated.

First and second housing components 22a, 22b define mirror-image configurations of one another and, when engaged to one another define a first, upper body portion 23a of housing 20. First, upper body portion 23a of housing 20 is formed via engagement of first and second housing components 22a, 22b, e.g., by snap-fit engagement, friction-fit engagement, adhesion, etc., and includes a proximal support 24a, an intermediate support 24b, and a distal support 24c. Third and fourth housing components 22c, 22d likewise define mirror-image configurations of one another and, when engaged to one another, define a second, lower body portion 23b of housing 20. Openings 25a are defined within first and second housing components 22a, 22b between intermediate support 24b, and a distal support 24c, and corresponding openings 25b are defined within third and fourth housing components 22c, 22d adjacent openings 25a such that, upon assembly of housing 20, openings 25a, 25b cooperate to define a window 25c on either side of housing 20, the importance of which are detailed below.

Proximal support 24a of first, upper body portion 23a defines a lumen formed by cooperating semi-cylindrical cut-outs 26a defined within first and second housing components 22a, 22b. Proximal support 24a further includes a finger 27a that is configured for mating engagement with a corresponding finger 27b of second, lower body portion 23b of housing 20 to releasably engage first and second body portions 23a, 23b to one another at the proximal ends thereof. Intermediate support 24b of first, upper body portion 23a defines a lumen formed by cooperating semi-cylindrical cut-outs 26b defined within first and second housing components 22a, 22b. Distal support 24c of first, upper body portion 23a also defines a lumen formed by cooperating semi-cylindrical cut-outs 26c defined within first and second housing components 22a, 22b.

Each of first and second housing components 22a, 22b includes a locking member 190 disposed on either side of distal support 24c of first, upper body portion 23a for enabling releasable engagement of first and second body portions 23a, 23b to one another at the distal ends thereof. Locking members 190 include engagement protrusions 192 defined at the free ends thereof that are configured for engagement within corresponding apertures 193 defined within second, lower body portion 23b of housing 20 and release buttons 196 that protrude from either side of first, upper body portion 23a of housing 20. Release buttons 196 are squeezable to urge protrusions 192 inwardly to disengage protrusions 192 from apertures 193 to permit selectively disengagement of first and second body portions 23a, 23b from one another at the distal ends thereof. First and second housing components 22a, 22b further include opposed recesses 28a defined on the respective interior surfaces thereof and opposed pivot members 28b extending inwardly from recesses 28a into first, upper body portion 23a and towards one another. As detailed below, pivot members 28b are configured to pivotably engage trigger 62 of trigger assembly 60 with housing 20.

Second, lower body portion 23b of housing 20 is formed via third and fourth housing components 22c, 22d, respectively, e.g., by snap-fit engagement, friction-fit engagement, adhesion, etc., and includes a fixed handle 50 extending therefrom. As noted above, second, lower body portion 23b of housing 20 includes a finger 27b disposed at the proximal end thereof that is configured to releasably engage finger 27a of first, upper body portion 23a to releasably engage first and second body portions 23a, 23b to one another at the respective proximal ends thereof, and a pair of apertures 193 that are configured to receive corresponding engagement protrusions 192 of locking members 190 of first, upper body portion 23a to releasably engage first and second body portions 23a, 23b to one another at the respective distal ends thereof. Second, lower body portion 23b of housing 20 further includes a cylindrical recess 29 formed within the inwardly-facing surface of each of third and fourth housing components 22c, 22d. Recesses 29 are configured to receive pivot members 45 of movable handle 40 of handle assembly 30 to pivotably couple movable handle 40 with housing 20, as detailed below.

Fixed handle 50 of second, lower body portion 23b, which forms part of handle assembly 30, detailed below, supports activation button 18 and is configured to receive cable 14 of electrical connector assembly 12. As noted above, electrical connector assembly 12 is configured to connect to the source of energy (not shown) for providing energy to forceps 10 via electrical leads 15 housed therein. More specifically, one or more of the electrical leads 15 disposed within cable 14 extends through fixed handle 50 to operably couple activation button 18 to the source of energy (not shown), one or more of the electrical leads 15 extends through fixed handle 50 into second, lower body portion 23b and through outer shaft 90 to ultimately couple electrically-conductive tissue-contacting surface 112 of pivoting jaw member 110 (see FIGS. 3A and 3B) to the source of energy (not shown), one or more of the electrical leads 15 extends through fixed handle 50 into second, lower body portion 23b and through outer shaft 90 to ultimately couple electrically-conductive tissue-contacting surface 122 of translating jaw member 120 (see FIGS. 3A and 3B) to the source of energy (not shown), and one or more of the electrical leads 15 extends through fixed handle 50 into second, lower body portion 23b and through outer shaft 90 to ultimately couple electrical cutting element 124 of translating jaw member 120 (see FIGS. 3A and 3B) to the source of energy (not shown).

Handle assembly 30 generally includes a movable handle 40 and a fixed handle 50 that, as mentioned above, extends from second, lower body portion 23b of housing 20. Movable handle 40 includes a lever 42 defining a finger hole 43 and a bifurcated neck 44 extending upwardly from lever 42 and into second, lower body portion 23b of housing 20. Each bifurcated portion of neck 44 is pivotably coupled to the adjacent housing component 22c, 22d of second, lower body portion 23b by a pivot member 45 such that movable handle 40 is pivotable relative to fixed handle 50 between an initial position, wherein movable handle 40 is spaced-apart from fixed handle 50, and a compressed position, wherein movable handle 40 is positioned in close proximity to fixed handle 50. Each bifurcated portion of neck 44 includes an extension 46 extending proximally therefrom. Extensions 46 are pivotably coupled to corresponding linkage members 48 at the first ends of linkage members 48 via a floating pivot 49. The second ends of linkage members 48 are engaged to one another via a transverse pin 51 extending therebetween. The ends of transverse pin 51 are received within longitudinally-extending recesses (not shown) defined within third and fourth housing components 22c, 22d of housing 20 to confine transverse pin 51 to longitudinal movement relative to housing 20. As a result of this configuration, pivoting of movable handle 40 from the initial position to the compressed position urges transverse pin 51 to translate proximally relative to housing 20, while return of movable handle 40 from the compressed position to the initial position pulls transverse pin 51 to translate distally relative to housing 20.

Lever 42 of movable handle 40 includes a projection 53 extending proximally therefrom that is positioned such that, once the compressed position of movable handle 40 has been reached, projection 53 is urged into contact with activation button 18 sufficiently so as to activate activation button 18. Activation of activation button 18, as detailed below, initiates the supply of energy from the source of energy (not shown) to tissue-contacting surface 112 of pivoting jaw member 110, tissue-contacting surface 122 of translating jaw member 120, and/or electrical cutting element 124 for treating and/or cutting tissue (see FIGS. 3A and 3B).

Trigger assembly 60 includes a trigger 62 having a toggle member 63 and an arm 64 extending upwardly from toggle member 63 and into housing 20. Arm 64 includes a bifurcated portion 65 disposed within second, lower body portion 23b of housing 20. Bifurcated portion 65 defines a window 66 between the bifurcated portions thereof and includes first and second pivot members 67 that extend inwardly from either side of bifurcated portion 65 into window 66. A finger 68 extends from arm 64 into first, upper body portion 23a of housing 20. A free end of finger 68 defines a transverse bore 69 that is configured to receive pivot members 28b of first, upper body portion 23a of housing 20 to pivotably couple trigger 62 to housing 20. Thus, upon pivoting of trigger 62 about pivot members 28b and relative to housing 20 from an un-actuated position to an actuated position, bifurcated portion 65 of trigger 62 is urged proximally. On the other hand, return of trigger 62 from the actuated position back to the un-actuated position urges bifurcated portion 65 of trigger 62 distally.

Transmission assembly 80, as noted above, includes outer shaft 90, end effector assembly 100, first drive assembly 130, second drive assembly 160, and rotating assembly 170. Outer shaft 90 includes a proximal portion 92 that extends into housing 20 and a distal portion 94 that operably supports pivoting jaw member 110 of end effector assembly 100. Proximal portion 92 of outer shaft 90, more specifically, extends through the lumen formed by cooperating semi-cylindrical cut-outs 26c of distal support 24c of first, upper body portion 23a of housing 20. Spaced-apart proximal and distal cuffs 95a, 95b are disposed about proximal portion 92 of outer shaft 90 on either side of the lumen formed by cooperating semi-cylindrical cut-outs 26c of distal support 24c so as to longitudinally fix outer shaft 90 relative to housing 20 while still permitting outer shaft 90 to rotate relative to housing 20. A pair of opposed, longitudinally extending slots 96 are defined through outer shaft 90 on either side thereof, proximally of cuffs 95a, 95b. Slots 96 are positioned adjacent windows 25c defined on either side of housing 20. Proximal portion 92 of outer shaft 90 further includes a biasing member 97 disposed thereabout and positioned adjacent windows 25c between intermediate and distal supports 24b, 24c of first, upper body portion 23a of housing 20. Distal portion 94 of outer shaft 90 includes a bifurcated distal extension 98 extending from the distal end of outer shaft 90. Bifurcated distal extension 98 includes a pair of spaced-apart supports 99a that each define an aligned, transverse aperture 99b extending therethrough, and a longitudinal cam track 99c defined on the inwardly-facing surface thereof.

With additional reference to FIGS. 3A and 3B, end effector assembly 100 is operably coupled to bifurcated distal extension 98 of outer shaft 90 and includes a pivoting jaw member 110 and a translating jaw member 120. Pivoting jaw member 110 includes a distal jaw body 110a and a pair of spaced-apart proximal flanges 110b extending proximally from distal jaw body 110a. Distal body 110a includes an electrically-insulative outer jaw housing 111, and an electrically-conductive tissue-contacting surface 112 that opposes translating jaw member 120. Tissue-contacting surface 112 may define a semi-oval cross-sectional configuration, or other suitable configuration that is complementary to the electrically-conductive tissue-contacting surface 122 of translating jaw member 110. Alternatively, both tissue-contacting surfaces 112, 122 of jaw members 110, 120 may define linear configurations or other non-complementary configurations. Tissue-contacting surface 112 of pivoting jaw member 110, as mentioned above, is adapted to connect to the source of energy (not shown), e.g., via one or more of the electrical leads 15.

Proximal flanges 110*b* of pivoting jaw member 110 each include a pivot member 114 extending outwardly therefrom that is configured for receipt within the aperture 98 defined within the corresponding support 99*a* of bifurcated distal extension 98 of outer shaft 90 to pivotably couple pivoting jaw member 110 to outer shaft 90. Proximal flanges 110*b* each further define a drive slot 115 that is angled relative to the cam track 99*c* of the corresponding support 99*a* of bifurcated distal extension 98 of outer shaft 90. As detailed below, drive slots 115 enable the coupling of pivoting jaw member 110 to first drive shaft 132 of first drive assembly 130 such that translation of first drive shaft 132 through outer shaft 90 and relative to pivoting jaw member 110 effects pivoting of pivoting jaw member 110 relative to translating jaw member 120 between a spaced-apart position and an approximated position for grasping tissue therebetween.

Translating jaw member 120 of end effector assembly 100 is formed with or otherwise engaged to second drive bar 162 of second drive assembly 160 and extends distally therefrom. Translating jaw member 120 includes a jaw body 121 having an electrically-conductive tissue-contacting surface 122 that is initially positioned to oppose tissue-contacting surface 112 of pivoting jaw member 110. Jaw body 121 may define an oval-shaped cross-sectional configuration that is complementary to that of tissue-contacting surface 112 such that jaw body 121 is at least partially received within jaw member 110 in the approximated position of end effector assembly 100, only tissue-contacting surface 122 of translating jaw member 120 may be complementary to tissue-contacting surface 112 of pivoting jaw member 110, or non-complementary configurations may be provided. As detailed below, translating jaw member 120 is translatable between a distal position (FIG. 7B), wherein tissue-contacting surfaces 112, 122 of jaw members 110, 120 are aligned with one another, and a proximal position (FIG. 7C), wherein tissue-contacting surface 122 of translating jaw member 120 is proximally offset relative to tissue-contacting surface 112 of pivoting jaw member 110. In the proximal position (FIG. 7C), between 25% and 75% of the tissue-contacting surfaces 112, 122 may be longitudinally offset, e.g., non-overlapping. In some embodiments, in the proximal position (FIG. 7C), 50% of each of the tissue-contacting surfaces 112, 122 is longitudinally offset relative to the other tissue-contacting surface 112, 122.

Tissue-contacting surface 122 of translating jaw member 120, as mentioned above, is adapted to connect to the source of energy (not shown), e.g., via one or more of the electrical leads 15. In one particular configuration, for example, end effector assembly 100 defines a bipolar configuration wherein tissue-contacting surface 112 is configured to be charged to a first electrical potential and tissue-contacting surface 122 is configured to be charged to a second, different electrical potential such that an electrical potential gradient is created for conducting energy between surfaces 112, 122 and through tissue grasped therebetween for treating e.g., sealing, tissue. However, other suitable configurations such as monopolar configurations or configurations utilizing other forms of energy, e.g., thermal energy, ultrasonic energy, light energy, etc., are also contemplated.

Translating jaw member 120 further includes an electrical cutting element 124 incorporated into jaw body 121 at the distal end thereof. At least a portion of electrical cutting element 124 is positioned to oppose pivoting jaw member 110 and such portion (or the entirety) of electrical cutting element 124 may define a configuration wherein electrical cutting element 124 narrows to an apex in the distal-to-proximal direction, although other suitable configurations are also contemplated. Electrical cutting element 124 defines a reduced width as compared to tissue-contacting surface 122 and is at least partially surrounded by tissue-contacting surface 122. Further, electrical cutting element 124 is electrically-insulated from tissue-contacting surface 122 via an insulation layer 126 and is independently adapted to connect to the source of energy (not shown), e.g., via one or more of the electrical leads 15. As detailed below, electrical cutting element 124 may be energized to facilitate dynamic electrical cutting of tissue in either a bipolar mode or a monopolar mode. Further, upon movement from the distal position (FIG. 7B) to the proximal position (FIG. 7C), electrical cutting element 124 may be configured to travel between 25% and 75% of the length of tissue-contacting surface 112 of pivoting jaw member 110, depending upon the degree to which surface 122 is offset relative to surface 112 in the proximal position of translating jaw member 120 (FIG. 7C). Using the example above where translating jaw member 120 is translated such that, when disposed in the proximal position (FIG. 7C), 50% of each of the tissue-contacting surfaces 112, 122 is offset relative to the other tissue-contacting surface 112, 122, electrical cutting element 124 would travel longitudinally along 50% of the length of tissue-contacting surface 112.

First drive assembly 130 includes a first drive bar 132 that is slidably disposed within outer shaft 90 and, as mentioned above, is operably coupled to pivoting jaw member 110 of end effector assembly 100. First drive bar 132 includes a bifurcated distal extension 134 disposed at the distal end of first drive bar 132. Bifurcated distal extension 134 includes a pair of spaced-apart supports 136 that each includes a pivot member 138 extending outwardly therefrom. Pivot members 138 extend through respective drive slots 115 of pivoting jaw member 110 and are received within longitudinal cam tracks 99*c* defined within supports 99*a* of bifurcated distal extension 98 of outer shaft 90 to guide translation of first drive shaft 132 through outer shaft 90. First drive shaft 132 is translatable through outer shaft 90 and relative to pivoting jaw member 110 between distal and proximal positions for translating pivot members 138 through drive slots 115 and longitudinal cam tracks 99*c* to urge pivoting jaw member 110 to pivot relative to translating jaw member 120 between spaced-apart and approximated positions, respectively.

First drive bar 132 of first drive assembly 130 extends proximally through outer shaft 90 and into housing 20. A mandrel 140 is slidably disposed about first drive bar 132 within housing 20 towards the proximal end of first drive bar 132. Mandrel 140 defines an annular slot 141 configured to receive transverse pin 51 of handle assembly 30 such that movable handle 40 may be selectively actuated to translate first drive bar 132 relative to outer shaft 90 and, thus, to pivot pivoting jaw member 110 between the spaced-apart and approximated positions (FIGS. 7A and 7B, respectively). A sleeve 142 slidably disposed about first drive bar 132 is fixedly engaged to mandrel 140 and extends distally from mandrel 140. Sleeve 142 includes a first collar 144 engaged thereto at the distal end thereof. A second collar 146 is slidably disposed about sleeve 142 and is positioned between mandrel 140 and first collar 144. Second collar 146 is fixed to first drive bar 132 via a pin 147 extending through a slot defined within sleeve 142 and through an aperture 139 defined within first drive bar 132. A biasing member 148 is disposed about sleeve 142 between first and second collars 144, 146, respectively, so as to bias second collar 146 distally, thereby biasing first drive bar 132 distally relative to outer shaft 90. As a result of this distal bias of first drive bar 132, pivoting jaw member 110 is biased towards the spaced-apart position relative to translating jaw member 120. First drive bar 132 further includes a pair of opposed, longitudinally extending slots 150 defined therethrough, the importance of which is detailed below.

Second drive assembly 160 includes a second drive bar 162 that is slidably disposed within first drive bar 132 and, as mentioned above, has translating jaw member 120 of end effector assembly 100 formed therewith and extending distally therefrom. Second drive bar 162 defines a transverse lumen 164 extending therethrough towards the proximal end thereof.

Rotating assembly 170 includes a rotation wheel 172, a distal collar 174 disposed distally of rotation wheel 172 and formed with or otherwise coupled to rotation wheel 172, and a proximal hub 176 disposed proximally of rotation wheel 172 and formed with or otherwise coupled to rotation wheel 172. Rotation wheel 172 is mounted about second drive bar 162 of second drive assembly 160 via a transverse pin 166 (FIG. 4) extending through distal collar 174 of rotation wheel 172, longitudinal slots 96, 150 of outer shaft 90 and first drive bar 132, respectively, and transverse lumen 164 of second drive bar 162. Rotation wheel 172 extends through windows 25c defined within housing 20 on either side thereof to enable manual manipulation of rotation wheel 172 for rotating rotation wheel 172 relative to housing 20, thereby rotating first and second drive bars 132, 162, respectively, outer shaft 90, and end effector assembly 100 relative to housing 20.

Proximal hub 176 of rotating assembly 170 is configured for positioning within window 66 of bifurcated portion 65 of trigger 62 and defines an annular slot 178 that is configured to receive pivot members 67 of bifurcated portion 66 such that pivoting of trigger 62 about pivot member 28b and relative to housing 20 from the un-actuated position to the actuated position pulls bifurcated portion 65 proximally to thereby pull proximal hub 176 proximally, and such that return of trigger 62 from the actuated position back to the un-actuated position urges bifurcated portion 65 distally, thereby urging proximal hub 176 distally. As a result of proximal hub 176 being formed with or otherwise coupled to rotation wheel 172 and rotation wheel 172 being mounted about second drive bar 162, pivoting of trigger 62 from the un-actuated position to the actuated position translates rotation wheel 172 proximally through window 25c of housing 20, second drive bar 162 proximally through first drive bar 132, and jaw member 120 proximally relative to pivoting jaw member 110 from the distal position (FIG. 7B) to the proximal position (FIG. 7C), while return of trigger 62 from the actuated position back to the un-actuated position translates rotation wheel 172 distally through window 25c of housing 20, second drive bar 162 distally through first drive bar 132, and jaw member 120 distally relative to pivoting jaw member 110 from the proximal position (FIG. 7C) to the distal position (FIG. 7B). Biasing member 97 of outer shaft 90 is positioned between intermediate support 24b of first, upper body portion 23a of housing 20 and proximal hub 176 of rotating assembly 170 so as to bias rotating assembly 170 proximally, thereby biasing trigger 62 towards the un-actuated position, and translating jaw member 120 towards the distal position (FIG. 7B).

Figure 4:
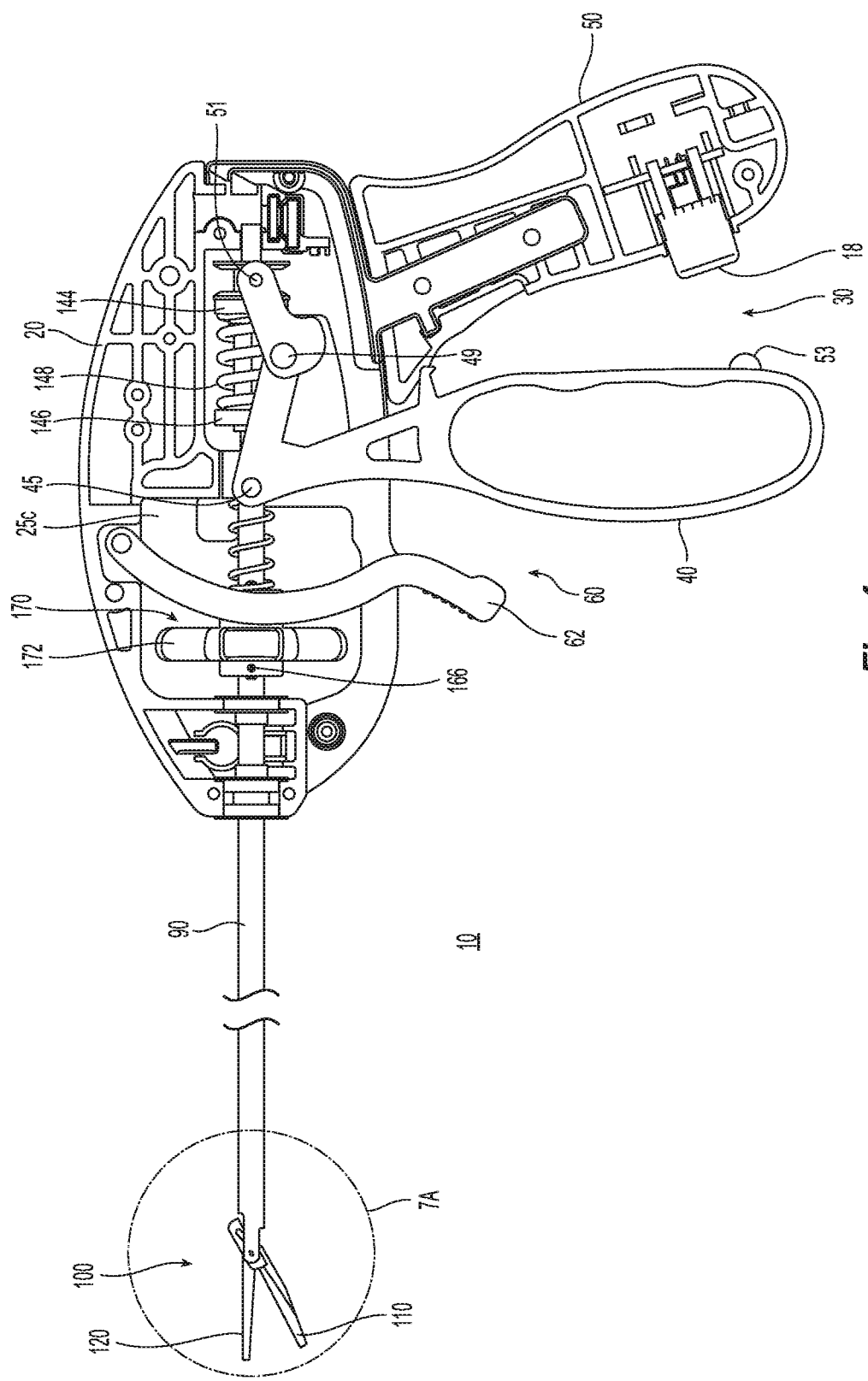
FIG. 4 is a side view of the forceps of FIG. 1 with a portion of the housing removed to illustrate the internal components thereof, wherein the forceps is disposed in a first position.
Figure 5:
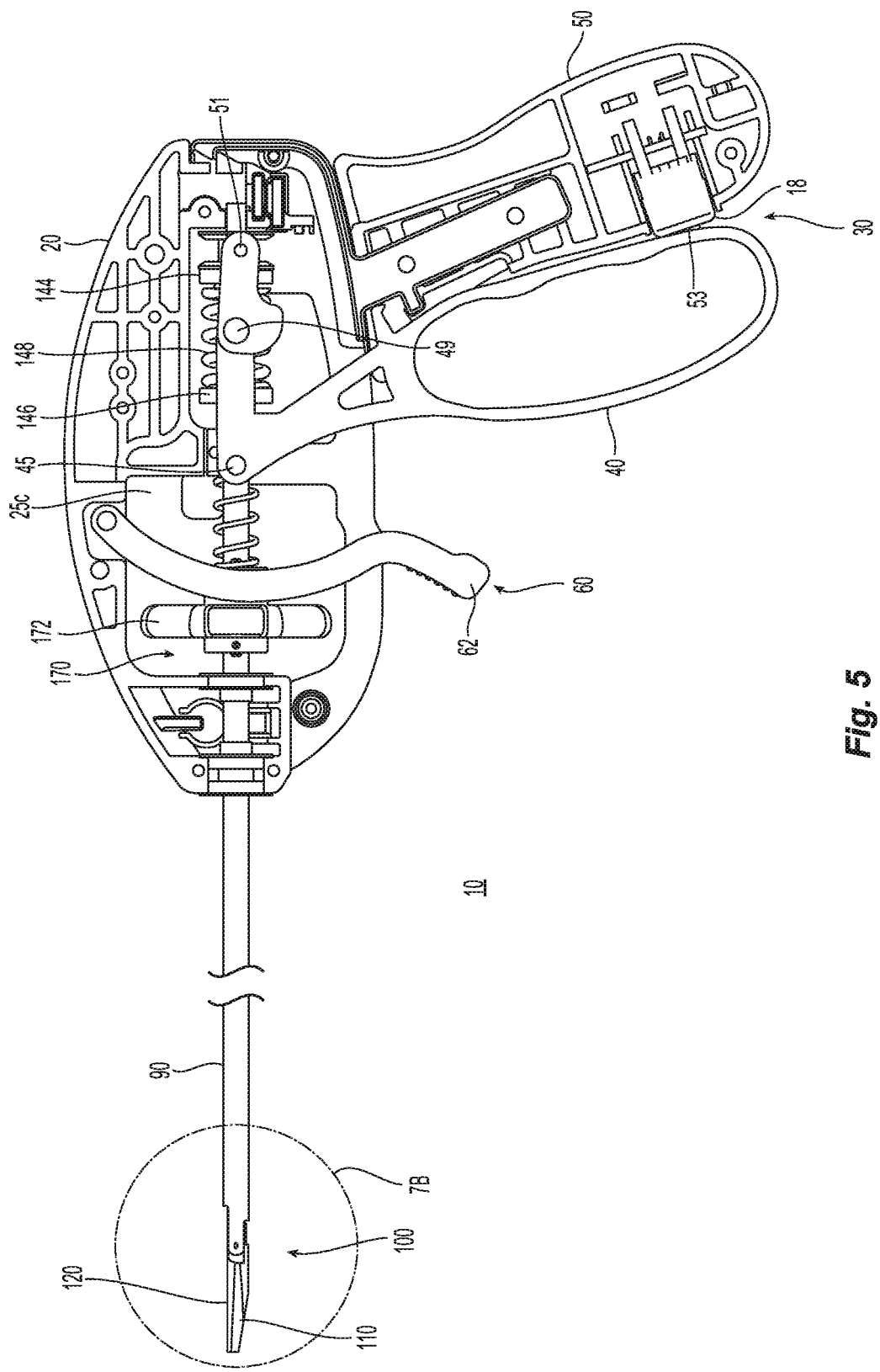
FIG. 5 is a side view of the forceps of FIG. 1 with a portion of the housing removed to illustrate the internal components thereof, wherein the forceps is disposed in a second position.

With reference to FIGS. 4-7C, the use and operation of forceps 10 for grasping, treating, and/or cutting tissue is detailed. Initially, as shown in FIGS. 4 and 7A, jaw members 110, 120 are disposed in the spaced-apart position and, correspondingly, movable handle 40 is disposed in the initial position. Further, at this point, translating jaw member 120 is disposed in the distal position and, correspondingly, trigger 62 is disposed in the un-actuated position. At this point, forceps 10 may be manipulated and/or end effector assembly 100 may be rotated, e.g., via rotating rotation wheel 172 relative to housing 20, such that tissue to be grasped, treated, and/or cut is disposed between jaw members 110, 120. Once positioned as desired, movable handle 40 is pivoted from the initial position towards the compressed position to approximate jaw members 110, 120 about tissue and grasp tissue therebetween, as shown in FIGS. 5 and 7B. As movable handle 40 reaches the compressed position, jaw members 110, 120 impart an appropriate grasping pressure on tissue disposed therebetween, e.g., as a result of the disposition of biasing member 148 between first and second collars 144, 146, respectively (see FIG. 2). Further, as movable handle 40 reaches the compressed position, an over-center locking position of floating pivots 49 relative to pivot members 45 and transverse pin 51 (see FIG. 5) is achieved, thus retaining movable handle 40 in the compressed position and, jaw members 110, 120 in the approximated position.

Once the compressed position has been reached, projection 53 of movable handle 40 is urged into contact with activation button 18 sufficiently so as to activate activation button 18. Activation of activation button 18, as mentioned above, initiates the supply of energy from the source of energy (not shown) to surfaces 112, 122 of jaw members 110, 120. As such, energy is conducted between surfaces 112, 122 and through tissue grasped therebetween to treat, e.g., seal, tissue. During the conduction of energy between surfaces 112, 122 of jaw members 110, 120 to treat tissue, electrical cutting element 124 may be energized to the same potential as surface 122 or may remain un-energized. Further, the supply of energy to surfaces 112, 122 upon activation of activation button 18 may be controlled according to an algorithm stored in the source of energy (not shown), e.g., a generator, or in any other suitable manner, including feedback based control. Once a desired tissue treatment, e.g., sealing, has been achieved, the supply of energy to surfaces 112, 122 may be automatically cut-off, in accordance with the algorithm, regardless of the condition of activation button 18, although other configurations are also contemplated.

Figure 6:
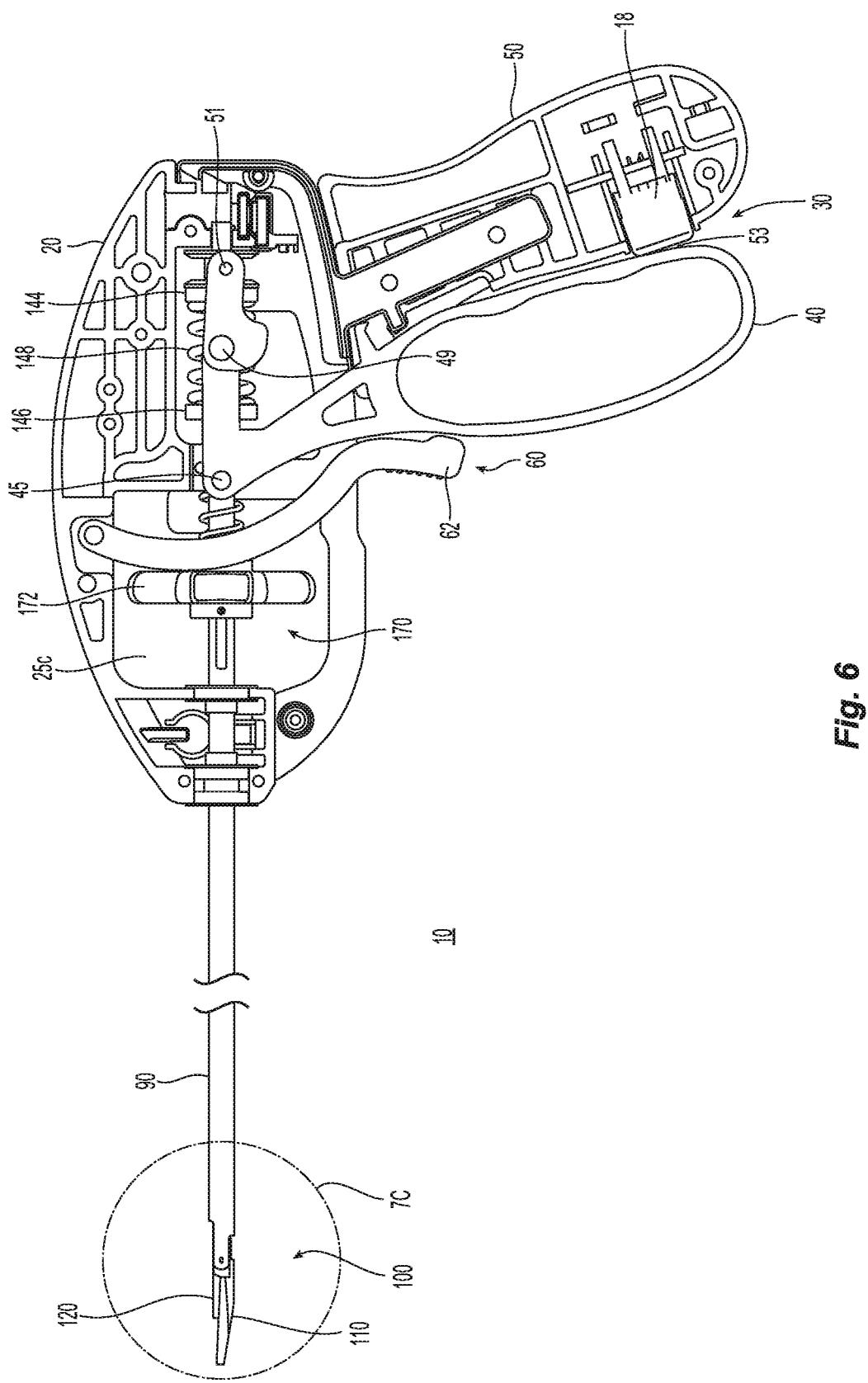
FIG. 6 is a side view of the forceps of FIG. 1 with a portion of the housing removed to illustrate the internal components thereof, wherein the forceps is disposed in a third position.

Referring to FIGS. 5, 6, 7B and 7C, once tissue has been treated, or where it is only desired to cut tissue, while maintaining movable handle 40 locked in the compressed position, trigger 62 may be pivoted from the un-actuated position to the actuated position to translate rotation assembly 170, second drive bar 162 and, thus, translating jaw member 120 proximally relative to pivoting jaw member 110 and tissue disposed therebetween from the distal position (FIGS. 5 and 7B) to the proximal position (FIGS. 6 and 7C). Upon the initial actuation of trigger 62 (as determined via a sensor (not shown) that monitors movement of trigger 62, a sensor (not shown) that monitors the relative position of jaw members 110, 120, or other suitable sensor); after a pre-determined amount of time from activation of activation button 18; upon sensing completion of the desired tissue treatment, e.g., sealing; upon activation of an independent activation button (not shown); or via any other suitable mechanism, energy is supplied to electrical cutting element 124 such that, as translating jaw member 120 (which includes electrical cutting element 124) is translated proximally relative to tissue and pivoting jaw member 110, dynamic electrical tissue cutting is effected via the translation of electrically cutting element 124 relative to tissue.

With electrical cutting element 124 energized for dynamic electrical tissue cutting, surfaces 112, 122 may be turned off, e.g., not energized, such that electrical cutting element 124 operates in a monopolar fashion, or either or both of surfaces 112, 122 may be energized to an opposite potential as that of electrical cutting element 124 such that electrical cutting element 124 and surface 112 and/or surface 122 cooperate to function in a bipolar fashion. Upon completion of dynamic electrical tissue cutting, e.g., upon jaw member 120 reaching the proximal position as determined via one or more sensors (not shown, such as those mentioned above), the supply of energy to electrical cutting element 124 is turned off. Thereafter, trigger 62 may be released or returned to the unactuated position to return translating jaw member 120 distally to the distal position. Alternatively, the supply of energy to electrical cutting element 124 may be maintained during return of translating jaw member 120 to the distal position, and thereafter turned off. Once translating jaw member 120 has been returned to the distal position, movable handle 40 may be urged distally towards the initial position to disengage the over-center lock and allow movable handle 40 to return to the initial position, thereby returning pivoting jaw member 110 to the spaced-apart position relative to translating jaw member 120.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 8:
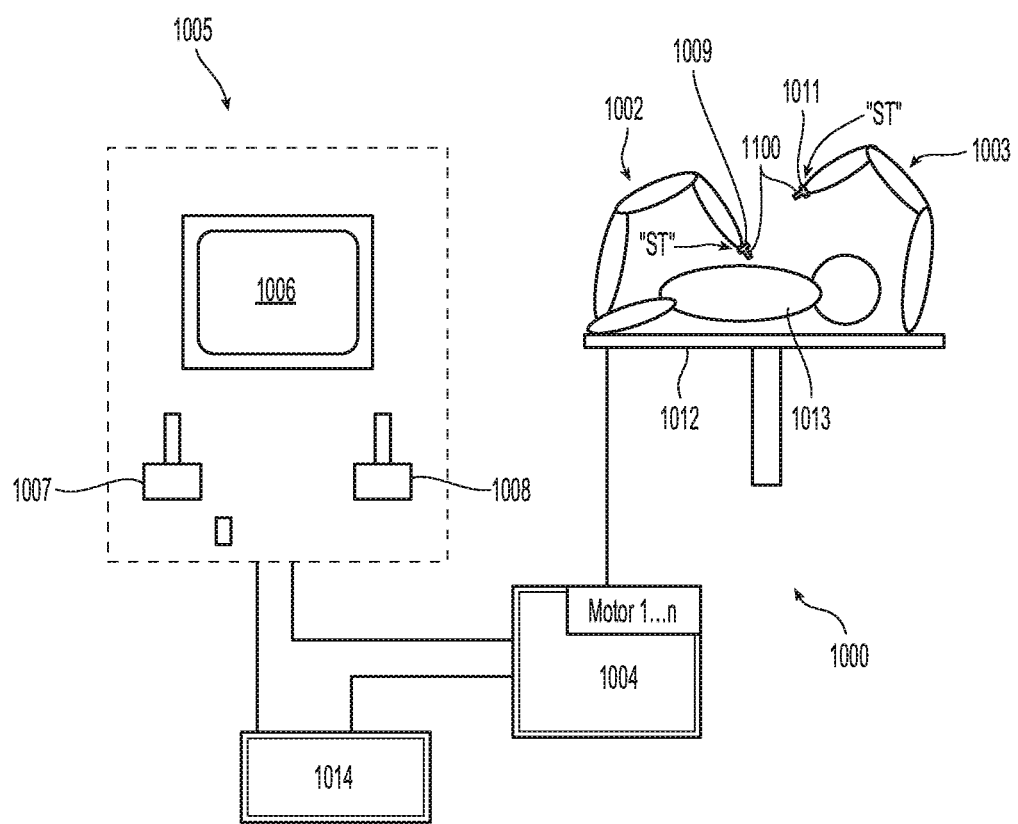
FIG. 8 is a schematic illustration of a robotic system configured for use in accordance with the present disclosure.

Referring to FIG. 8, a medical work station is shown generally as work station 1000 and may generally include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of the embodiments disclosed hereinabove.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
an end effector assembly, including:
first and second jaw members, each jaw member including an opposed electrically-conductive tissue-contacting surface, the first jaw member pivotable relative to the second jaw member between a spaced-apart position and an approximated position for grasping tissue between the opposed electrically-conductive tissue-contacting surfaces, the first jaw member pivotally supported by a first proximal flange and a second proximal flange, the second jaw member including an electrical cutting element, wherein when in the approximated position, the second jaw member is translatable relative to the first jaw member between a first position, wherein the opposed electrically-conductive tissue-contacting surfaces are longitudinally aligned with one another, and a second position, wherein the opposed electrically-conductive tissue-contacting surfaces are longitudinally offset relative to one another, wherein the second jaw member is translated between the first and second positions between the first proximal flange and the second proximal flange of the first jaw member, wherein, upon translation of the second jaw member between the first and second positions, the electrical cutting element is translated at least partially along the opposed electrically-conductive tissue-contacting surface of the first jaw member.

2. The forceps according to claim 1, wherein the opposed electrically-conductive tissue-contacting surfaces of the first and second jaw members are adapted to connect to a source of energy for conducting energy through tissue grasped therebetween to treat tissue.

3. The forceps according to claim 1, wherein the electrical cutting element is adapted to connect to a source of energy for conducting energy through the tissue for dynamic electrical tissue cutting.

4. The forceps according to claim 3, wherein the electrical cutting element is configured for monopolar dynamic electrical tissue cutting.

5. The forceps according to claim 3, wherein the electrical cutting element and at least one of the opposed electrically-conductive tissue-contacting surfaces are configured for bipolar dynamic electrical tissue cutting.

6. The forceps according to claim 1, wherein the first and second jaw members define complementary configurations.

7. The forceps according to claim 6, wherein the second jaw member defines an oval cross-sectional shape and wherein the first jaw member defines a concave recess having a semi-oval cross-sectional shape, the concave recess of the first jaw member configured to at least partially receive the second jaw member in the approximated position of the first jaw member.

8. The forceps according to claim 1, wherein, in the second position of the second jaw member, between 25% and 75% of the opposed electrically-conductive tissue-contacting surfaces are disposed in non-overlapping relation relative to one another.

9. The forceps according to claim 1, wherein, in the second position of the second jaw member, 50% of the opposed electrically-conductive tissue-contacting surfaces are disposed in non-overlapping relation relative to one another.

10. A forceps, comprising:
a housing;
a shaft extending distally from the housing;
an end effector assembly disposed at a distal end of the shaft, the end effector assembly including first and second jaw members, each jaw member including an opposed electrically-conductive tissue-contacting surface, the first jaw member pivotable relative to the second jaw member between a spaced-apart position and an approximated position for grasping tissue between the opposed electrically-conductive tissue-contacting surfaces, the first jaw member pivotally supported by a first proximal flange and a second proximal flange, the second jaw member including an electrical cutting element, wherein when in the approximated position, the second jaw member translatable relative to the first jaw member between a first position, wherein the opposed electrically-conductive tissue-contacting surfaces are longitudinally aligned with one another, and a second position, wherein the opposed electrically-conductive tissue-contacting surfaces are longitudinally offset relative to one another, wherein the second jaw member is translated between the first and second positions between the first proximal flange and the second proximal flange of the first jaw member, wherein, upon translation of the second jaw member between the first and second positions, the electrical cutting element is translated at least partially along the opposed electrically-conductive tissue-contacting surface of the first jaw member;
a first drive assembly coupled to the first jaw member, the first drive assembly selectively operable to pivot the first jaw member relative to the second jaw member between the spaced-apart and approximated positions; and
a second drive assembly coupled to the second jaw member, the second drive assembly selectively operable to translate the second jaw member relative to the first jaw member between the first and second positions.

11. The forceps according to claim 10, further including a handle assembly associated with the housing and operably coupled to the first drive assembly, the handle assembly including a movable handle movable between an initial position and a compressed position to pivot the first jaw member relative to the second jaw member between the spaced-apart and approximated positions.

12. The forceps according to claim 10, further including a trigger assembly associated with the housing and operably coupled to the second drive assembly, the trigger assembly including a trigger movable between an un-actuated position and an actuated position to translate the second jaw member relative to the first jaw member between the first and second positions.

13. The forceps according to claim 10, further including a rotating assembly coupled to the first and second drive assemblies and the shaft, the rotating assembly including a rotation wheel selectively rotatable relative to the housing for rotating the shaft and end effector assembly relative to the housing.

14. The forceps according to claim 10, wherein the opposed electrically-conductive tissue-contacting surfaces of the first and second jaw members are adapted to connect to a source of energy for conducting energy through tissue grasped therebetween to treat tissue.

15. The forceps according to claim 14, further including an activation button disposed on the housing, the activation button selectively actuatable for initiating the supply of energy to the opposed electrically-conductive tissue-contacting surfaces of the first and second jaw members.

16. The forceps according to claim 10, wherein the electrical cutting element is adapted to connect to a source of energy for conducting energy through tissue for dynamic electrical tissue cutting.

17. The forceps according to claim 16, wherein the electrical cutting element is configured for monopolar dynamic electrical tissue cutting.

18. The forceps according to claim 16, wherein the electrical cutting element and at least one of the opposed electrically-conductive tissue-contacting surfaces are configured for bipolar dynamic electrical tissue cutting.

19. The forceps according to claim 10, wherein, in the second position of the second jaw member, between 25% and 75% of the opposed electrically-conductive tissue-contacting surfaces are disposed in non-overlapping relation relative to one another.

20. The forceps according to claim 10, wherein, in the second position of the second jaw member, 50% of the opposed electrically-conductive tissue-contacting surfaces are disposed in non-overlapping relation relative to one another.

* * * * *